(12) United States Patent
Jung et al.

(10) Patent No.: US 12,708,562 B2
(45) Date of Patent: Aug. 18, 2026

(54) ADJUSTABLE LASER PULSE CONTROL

(71) Applicant: Alcon Inc., Fribourg (CH)

(72) Inventors: David Jung, Tustin, CA (US); Alireza Malek Tabrizi, Irvine, CA (US); Keith Watanabe, Irvine, CA (US)

(73) Assignee: Alcon, Inc., Fribourg (CH)

( * ) Notice: Subject to any disclaimer, the term of this patent is extended or adjusted under 35 U.S.C. 154(b) by 366 days.

(21) Appl. No.: 18/308,150

(22) Filed: Apr. 27, 2023

(65) Prior Publication Data

US 2023/0363944 A1 Nov. 16, 2023

Related U.S. Application Data

(60) Provisional application No. 63/364,430, filed on May 10, 2022.

(51) Int. Cl.
*A61F 9/008* (2006.01)
*A61B 18/00* (2006.01)

(52) U.S. Cl.
CPC .... *A61F 9/008* (2013.01); *A61B 2018/00696* (2013.01)

(58) Field of Classification Search
CPC ....................................................... A61F 9/008
See application file for complete search history.

(56) References Cited

U.S. PATENT DOCUMENTS 3,659,613 A * 5/1972 Bredemeier ......... B23K 26/032 606/3
6,322,554 B1 * 11/2001 Tomita .................... A61F 9/008 606/4
8,764,736 B2 7/2014 Kurtz
8,953,651 B2 2/2015 Karavitis
9,044,303 B2 6/2015 Kurtz et al.
9,931,447 B2 4/2018 Layser et al.
11,197,781 B2 12/2021 Wittnebel
2007/0073279 A1 3/2007 Rowe et al.
2007/0147730 A1 * 6/2007 Wiltberger ......... G02B 26/0816 385/16
2008/0015662 A1 1/2008 Tunnermann
2012/0136342 A1 5/2012 Bischoff et al.
2012/0245571 A1 * 9/2012 Mordaunt ............. H01S 5/0014 606/4
2012/0296319 A1 * 11/2012 Chaudhary ......... A61F 9/00825 606/4
2015/0230978 A1 8/2015 Vogler et al.
(Continued)

FOREIGN PATENT DOCUMENTS

WO 2009108543 A2 9/2009
WO 2023062565 A1 4/2023

*Primary Examiner* — Lynsey C Eiseman
(74) *Attorney, Agent, or Firm* — Patterson + Sheridan, LLP

(57) ABSTRACT

Systems and methods are disclosed for flexibly controlling laser pulses being output from a laser system. An example surgical system comprises a laser, an optical switching device, and a laser pulse controller. Optical switching control signals communicated by the laser pulse controller control the length of a pulse picking cycle and the number of laser pulses in each pulse picking cycle to be output from the laser system. The number of laser pulses in each pulse picking cycle to be output from the laser system may be adjustable in a range that includes more than 50% of the laser pulses in each pulse picking cycle.

10 Claims, 9 Drawing Sheets

(56) References Cited

U.S. PATENT DOCUMENTS

| | | | |
|---|---|---|---|
| 2018/0360657 | A1 | 12/2018 | Bor et al. |
| 2019/0201238 | A1 | 7/2019 | Bacher et al. |
| 2021/0135424 | A1 | 5/2021 | Bacher et al. |
| 2021/0145514 | A1 | 5/2021 | Grossman et al. |
| 2022/0354575 | A1 | 11/2022 | Jung |
| 2022/0354692 | A1 | 11/2022 | Bor et al. |
| 2023/0113339 | A1 | 4/2023 | Ovchinnikov |
| 2023/0116921 | A1 | 4/2023 | Jung et al. |
| 2023/0178953 | A1 | 6/2023 | Karim |
| 2023/0363945 | A1 | 11/2023 | Jung |

* cited by examiner

Top
Subrange 1
Subrange 2
Subrange 3
Bottom

100%
0%
Base Repetition Rate:
1 KHz Pulse from Laser

100%
0%
S
Pulse Picking Frequency: 100 Hz
Duty Ratio: 10%
Out: 1 Pulse Output Per
10 Laser Pulses 100%
0%
S
Pulse Picking Frequency: 100 Hz
Duty Ratio: 50%
Out: 5 Pulses Output Per
10 Laser Pulses 100%
0%
S
Pulse Picking Frequency: 100 Hz
Duty Ratio: 90%
Out: 9 Pulses Output Per
10 Laser Pulses

ADJUSTABLE LASER PULSE CONTROL

CROSS-REFERENCE TO RELATED APPLICATIONS

This application claims the benefit of priority of U.S. Provisional Patent Application Ser. No. 63/364,430 titled "ADJUSTABLE LASER PULSE CONTROL," filed on May 10, 2022, which is hereby incorporated by reference in its entirety as though fully and completely set forth herein.

TECHNICAL FIELD

The present disclosure is directed to systems and methods for controlling laser pulses being output from a laser system.

BACKGROUND

Lasers are used in many different medical procedures including a number of different ophthalmic procedures. For example, lasers may be used in cataract surgery, such as for fragmenting the cataractous lens. In some procedures, a laser is used for initial fragmentation of the lens, followed by phacoemulsification of the lens by an ultrasonic handpiece to complete the breakdown of the lens for removal. In other procedures, the laser may be used for complete fragmentation and/or phacoemulsification of the lens for removal, without the need for a separate application of ultrasonic energy. Lasers may also be used for other steps in cataract surgery, such as for making the corneal incision(s) and/or opening the capsule.

Lasers may also be used in glaucoma surgery. For example, a laser may be used to form all or part of a channel through the trabecular meshwork or scleral tissue for drainage of aqueous humor from the eye.

Lasers may also be used in vitreoretinal surgery. In some procedures, a laser may be used for vitrectomy, to sever or break the vitreous fibers for removal. The laser may be incorporated into a vitrectomy probe, and the energy from the laser may be applied to the vitreous fibers to sever or break the vitreous fibers for removal.

In other vitreoretinal applications, lasers may be used for photocoagulation of retinal tissue. Laser photocoagulation may be used to treat issues such as retinal tears and/or the effects of diabetic retinopathy.

U.S. Patent Application Publication No. 2018/0360657 discloses examples of an ophthalmic laser system. That application describes laser uses such as for forming surgical cuts or for photodisrupting ophthalmic tissue as well as for cataract surgery, such as laser-assisted cataract surgery (LACS). U.S. Patent Application Publication No. 2019/0201238 discloses other examples of an ophthalmic laser system. That application describes laser uses such as in a vitrectomy probe for severing or breaking vitreous fibers. U.S. Patent Application Publication No. 2018/0360657 and U.S. Patent Application Publication No. 2019/0201238 are expressly incorporated by reference herein in their entirety.

Some laser systems emit pulses, with the pulses having a desired duration and repetition rate. Operating a laser in pulses can achieve desirable power and energy characteristics for a particular application. In addition, while the energy of a beam emitted by a laser can be controlled by controlling the laser itself, in some systems it is desirable to control the amount of energy of a laser beam downstream from the laser. Existing systems for laser pulse selection typically have one or more drawbacks, such as power loss, complexity, cost, etc. There is a need for improved systems and methods for laser pulse control.

SUMMARY

The present disclosure is directed to improved systems and methods for controlling laser pulses being output from a laser system.

In some embodiments, a surgical system comprises: a laser configured to emit electromagnetic radiation in laser pulses, an optical switching device configured to switch between a first condition in which it allows laser pulses emitted from the laser to be output from the laser system and a second condition in which it prevents laser pulses emitted from the laser from being output from the laser system, and a laser pulse controller configured to communicate optical switching control signals to the optical switching device, wherein the optical switching control signals communicated by the laser pulse controller control the length of a pulse picking cycle and the number of laser pulses in each pulse picking cycle to be output from the laser system, and wherein the number of laser pulses in each pulse picking cycle to be output from the laser system is adjustable in a range that includes more than 50% of the laser pulses in each pulse picking cycle.

In some embodiments, the number of laser pulses in each pulse picking cycle to be output from the laser system may be adjustable in a range from 0% to 100% of the laser pulses in each pulse picking cycle. In some embodiments, when the laser system is set so that the number of laser pulses emitted by the laser in each pulse picking cycle is N, the number of laser pulses in each pulse picking cycle to be output from the laser system is adjustable in a range that includes 1 and N−1.

In some embodiments, the optical switching control signals communicated by the laser pulse controller comprise a first signal that controls the length of a pulse picking cycle and a second signal that controls the number of laser pulses in each pulse picking cycle to be output from the laser system. The first signal may be a sync signal.

In some embodiments, the optical switching device is further configured to control the amount of energy of the laser pulses emitted from the laser that is output from the laser system.

In some embodiments, the surgical system may further comprise an adjustable input device configured to be actuated over an operating range. The operating range of the adjustable input device may be configured to allow an operator to control dynamically the amount of energy of the laser pulses emitted from the laser that is output from the laser system. The operating range of the adjustable input device may be configured to allow an operator to control dynamically the percentage of laser pulses emitted from the laser that are output from the laser system. The adjustable input device may comprise a foot pedal configured to be actuated over the operating range.

In some embodiments, the optical switching device comprises a shutter and a shutter motor. The shutter motor may be configured to move the shutter in an alternating manner between a first position corresponding to the first condition of the optical switching device and a second position corresponding to the second condition of the optical switching device. The shutter may comprise a mirror. In some embodiments, the shutter has an axis of rotation and at least one open area and at least one solid area arranged around the axis of rotation of the shutter, wherein the shutter motor is configured to rotate the shutter around the axis of rotation of the shutter, wherein the first condition of the optical switching device corresponds to a position of the shutter in which a solid area of the shutter is not in a path of the laser pulses emitted from the laser, and wherein the second condition of the optical switching device corresponds to a position of the shutter in which a solid area of the shutter is in the path of the laser pulses emitted from the laser.

In some embodiments, the optical switching device may further comprise a laser energy control system configured to regulate the amount of electromagnetic energy of each laser pulse that exits the laser system. The laser energy control system may comprise: a waveplate, a waveplate motor, and a polarizer plate, wherein the waveplate motor is configured to move the waveplate into different positions corresponding to different percentages of laser electromagnetic energy permitted to pass through the laser energy control system. In some embodiments, the optical switching device comprises a pockels cell.

In some embodiments, a method of controlling a surgical system comprises: (i) providing input to the surgical system, wherein the surgical system comprises: a laser configured to emit electromagnetic radiation in laser pulses, an optical switching device configured to switch between a first condition in which it allows laser pulses emitted from the laser to be output from the laser system and a second condition in which it prevents laser pulses emitted from the laser from being output from the laser system, and a laser pulse controller configured to communicate optical switching control signals to the optical switching device, wherein the input to the surgical system comprises input that controls the length of a pulse picking cycle and the number of laser pulses in each pulse picking cycle to be output from the laser system, wherein the number of laser pulses in each pulse picking cycle to be output from the laser system is adjustable in a range that includes more than 50% of the laser pulses in each pulse picking cycle; (ii) emitting electromagnetic radiation from a laser in laser pulses; and (iii) outputting laser pulses from the laser system in accordance with the input that controls the length of a pulse picking cycle and the number of laser pulses in each pulse picking cycle to be output from the laser system.

In some embodiments, the step of outputting laser pulses from the laser system in accordance with the input comprises controlling the percentage of laser pulses emitted from the laser that are output from the laser system. In some embodiments, the step of outputting laser pulses from the laser system in accordance with the input comprises controlling the amount of energy of the laser pulses emitted from the laser that is output from the laser system.

Further examples and features of embodiments of the invention will be evident from the drawings and detailed description.

BRIEF DESCRIPTION OF THE DRAWINGS

The accompanying drawings illustrate example implementations of the systems and methods disclosed herein and, together with the description, serve to explain the principles of the present disclosure.

Figure 1:
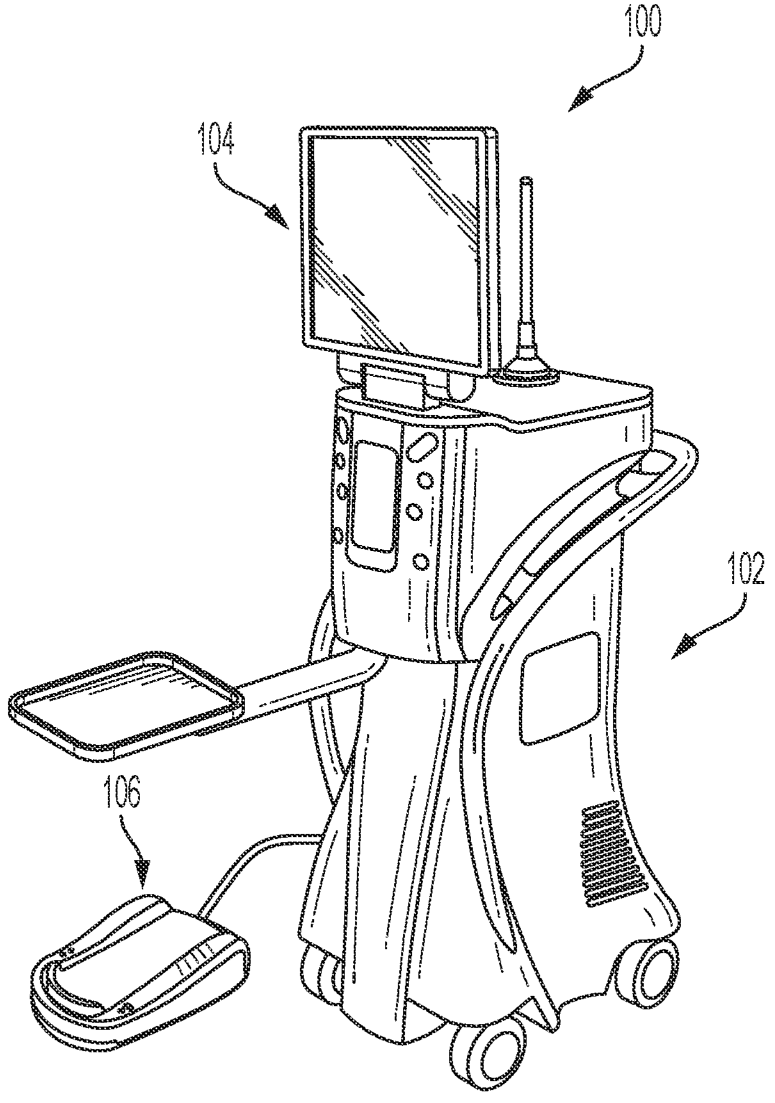
FIG. 1 shows an example ophthalmic surgical console with a foot pedal connected to it.

The accompanying drawings may be better understood by reference to the following detailed description.

DETAILED DESCRIPTION

For the purposes of promoting an understanding of the principles of the disclosure, reference will now be made to the implementations illustrated in the drawings, and specific language will be used to describe those implementations and other implementations. It will nevertheless be understood that no limitation of the scope of the claims is intended by the examples shown in the drawings or described herein. Any alterations and further modifications to the illustrated or described systems, devices, instruments, or methods, and any further application of the principles of the present disclosure, are fully contemplated as would normally occur to one skilled in the art to which the disclosure relates. In particular, the features, components, and/or steps described with respect to one implementation of the disclosure may be combined with features, components, and/or steps described with respect to other implementations of the disclosure. For simplicity, in some instances the same reference numbers are used throughout the drawings to refer to the same or like parts.

The designations "first" and "second" as used herein are not meant to indicate or imply any particular positioning or other characteristic. Rather, when the designations "first" and "second" are used herein, they are used only to distinguish one component from another. The terms "attached," "connected," "coupled," and the like mean attachment, connection, coupling, etc., of one part to another either directly or indirectly through one or more other parts, unless direct or indirect attachment, connection, coupling, etc., is specified.

FIG. 1 shows an example ophthalmic surgical console 100 with a foot pedal 106 connected to it. The example ophthalmic surgical console 100 may be used in systems and methods in accordance with the present disclosure. The ophthalmic surgical console 100 may be similar to ophthalmic surgical consoles as shown and described in U.S. Pat. No. 9,931,447, the entire disclosure of which is hereby expressly incorporated herein by reference. The ophthalmic surgical console 100 may be similar to ophthalmic surgical consoles that have been known and used, such as the CENTURION® Vision System available from Alcon Laboratories, Inc. (Fort Worth, Texas) or the CONSTELLATION® Vision System available from Alcon Laboratories, Inc. (Fort Worth, Texas), or any other ophthalmic surgical console suitable for use with the principles described herein.

As shown in FIG. 1, the example ophthalmic surgical console 100 includes a housing 102 with a computer system disposed therein and an associated display screen 104 showing data relating to system operation and performance during an ophthalmic surgical procedure.

The foot pedal 106 is an adjustable input device that an operator may actuate over an operating range for controlling one or more functions. The foot pedal 106 may be pressed downward to various positions over the operating range to control functioning as described further below. While a foot pedal 106 is shown, other adjustable input devices, such as hand-operated buttons or knobs, may be used. The foot pedal 106 or other adjustable input device may be connected to the surgical console 100 by a wired or wireless connection.

The surgical console 100 includes one or more systems that may be used in performing an ophthalmic surgical procedure. For example, the surgical console 100 may include a fluidics system that includes an irrigation system for delivering fluid to the eye and an aspiration system for aspirating fluid from the eye.

Figure 2:
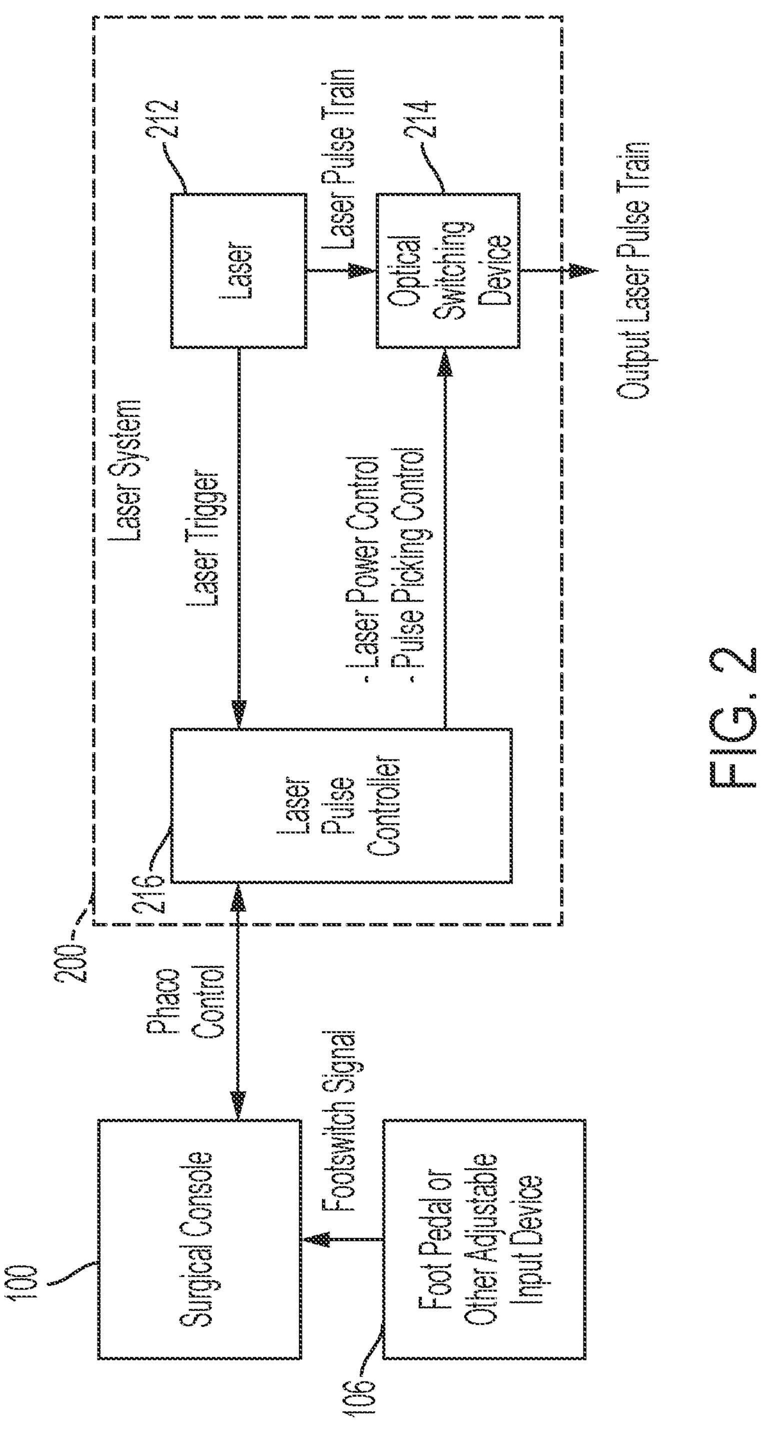
FIG. 2 shows an example of architecture for a surgical system comprising a laser system.

An example surgical system in accordance with this disclosure may include a laser system suitable for one or more ophthalmic procedures. FIG. 2 shows an example of architecture for a surgical system, including a surgical console 100, an adjustable input device, e.g., foot pedal 106, and an example laser system 200. The laser system 200 may comprise a laser 212, an optical switching device 214, and a laser pulse controller 216. In some embodiments, the laser system 200 may be housed within the surgical console 100. In other embodiments, the laser system 200 may be housed in a separate console that communicates with the surgical console 100. In other embodiments, one or more parts of the laser system 200, such as the laser 212 and optical switching device 214, may be housed in a separate console that communicates with the surgical console 100, and one or more other parts of the laser system 200, such as the laser pulse controller 216, may be housed in the surgical console 100. In other embodiments, the laser system 200 may be in a stand-alone housing that receives input from a foot pedal or other adjustable input device 106 without the need for a separate surgical console 100.

In addition to the laser 212, optical switching device 214, and laser pulse controller 216, the laser system 200 may have other components. For example, the laser system 200 may include components for operating the laser, such as a power supply, laser pumps, laser energy control, and monitor. In addition, the laser system 200 may include other components in the optical path of the laser output, such as one or more lenses, mirrors, and optical fibers (not shown).

In some embodiments, the laser system 200 may be suitable for cataract surgery. In some embodiments, the output energy of the laser system is suitable for fragmentation and/or emulsification a cataractous lens. In some examples, the laser output is used for fragmentation and/or phacoemulsification of the lens to a sufficient degree for removal of the lens.

In some embodiments, the laser system 200 may be suitable for glaucoma surgery. In some embodiments, the output energy of the laser system is suitable for making or facilitating the formation of a drainage channel in eye tissue.

The laser 212 may be any type of laser suitable for the desired application. The laser 212 may output suitable electromagnetic radiation at any suitable wavelength. For example, the laser 212 may emit electromagnetic radiation in one or more wavelengths in the visible, infrared, and/or ultraviolet wavelengths. The laser 212 may operate or be operated to emit a continuous beam of electromagnetic radiation. Alternatively, the laser 212 may operate or be operated to emit a pulsed beam.

In one example, the laser 212 operates in the infrared range. For example, the laser 212 may output electromagnetic radiation in the mid-infrared range, for example in a range of about 2.0 microns to about 4.0 microns. Some examples wavelengths include about 2.5 microns to 3.5 microns, such as about 2.775 microns, about 2.8 microns, or about 3.0 microns. Such a laser may be suitable, for example, for lens fragmentation in cataract surgery, or for other procedures.

The laser system 200 is designed to direct the laser electromagnetic radiation from the laser 212 to an output port. The laser system 200 may direct the laser electromagnetic radiation from the laser 212 to the output port through one or more optical components, such as lenses and mirrors.

An instrument may be optically connected to the laser system 200 to receive the laser electromagnetic radiation from the output port. The instrument may be, for example, a handpiece for an ophthalmic procedure. The instrument or handpiece may be connected to the laser system by a delivery optical fiber. The delivery optical fiber may be flexible and relatively long to give the operator flexibility in maneuvering the handpiece at some distance away from the laser system 200. The laser electromagnetic radiation may be transmitted from the laser system 200, through the optical fiber and handpiece, and from an output tip of the handpiece to the desired target, such as a lens or lens fragment in the eye of a patient.

The optical switching device 214 is a device that operates either to allow laser electromagnetic radiation, e.g., laser pulses, emitted from the laser 212 to be output from the laser system or to prevent laser electromagnetic radiation, e.g., laser pulses, emitted from the laser 212 from being output from the laser system. The optical switching device 214 may switch back and forth between these two conditions, under the control of the laser pulse controller 216.

In some examples, the optical switching device 214 may comprise a shutter and a shutter motor. Examples of suitable optical switching devices are described and illustrated in U.S. Provisional Patent Application No. 63/186,387, the entirety of which is hereby incorporated by reference herein, and in U.S. Provisional Patent Application No. 63/222,521, the entirety of which is hereby incorporated by reference herein.

For example, the optical switching device 214 may comprise a shutter that is moved by the shutter motor into and out of the path of laser electromagnetic radiation, to selectively allow or prevent laser electromagnetic radiation from being output from the laser system. The shutter motor may be configured to move the shutter in an alternating manner between a first position corresponding to a first condition of the optical switching device (in which it allows laser electromagnetic energy, e.g., laser pulses, emitted from the laser to be output from the laser system) and a second position corresponding to a second condition of the optical switching device (in which it prevents laser electromagnetic energy, e.g., laser pulses, emitted from the laser from being output from the laser system). In an example, the shutter comprises a mirror, and the shutter motor comprises a galvanometer motor.

In another example, the optical switching device 214 may comprise: (i) a shutter having an axis of rotation and at least one open area and at least one solid area arranged around the axis of rotation of the shutter, and (ii) a shutter motor configured to rotate the shutter around the axis of rotation of the shutter. In such an example, the first condition of the optical switching device (in which it allows laser electromagnetic energy, e.g., laser pulses, emitted from the laser to be output from the laser system) corresponds to a position of the shutter in which a solid area of the shutter is not in a path of the laser pulses emitted from the laser, and the second condition of the optical switching device (in which it prevents laser electromagnetic energy, e.g., laser pulses, emitted from the laser from being output from the laser system) corresponds to a position of the shutter in which a solid area of the shutter is in the path of the laser pulses emitted from the laser.

The optical switching device 214 may further comprise a laser energy control system configured to regulate the amount of electromagnetic energy of each laser pulse that exits the laser system. For example, the laser energy control system may comprise a waveplate, a waveplate motor, and a polarizer plate, wherein the waveplate motor is configured to move the waveplate into different positions corresponding to different percentages of laser electromagnetic energy permitted to pass through the laser energy control system. Examples of such laser energy control systems are described and illustrated in U.S. Provisional Patent Application No. 63/186,387, the entirety of which is hereby incorporated by reference herein, and in U.S. Provisional Patent Application No. 63/222,521, which, as mentioned above, are both incorporated by reference herein.

In another alternative embodiment, the optical switching device 214 may comprise a pockels cell. A pockels cell optical switching device may switch back and forth, under the control of the laser pulse controller 216, between a first condition in which it allows laser pulses emitted from the laser to be output from the laser system and a second condition in which it prevents laser pulses emitted from the laser from being output from the laser system. Also, a pockels cell optical switching device can be operated incrementally to allow different percentages of electromagnetic energy emitted by the laser to be output by the laser system.

The laser pulse controller 216 is configured to communicate optical switching control signals to the optical switching device 214. The optical switching control signals are based on inputs to the surgical system, including from the adjustable input device, e.g., foot pedal 106, if provided.

Figure 3:
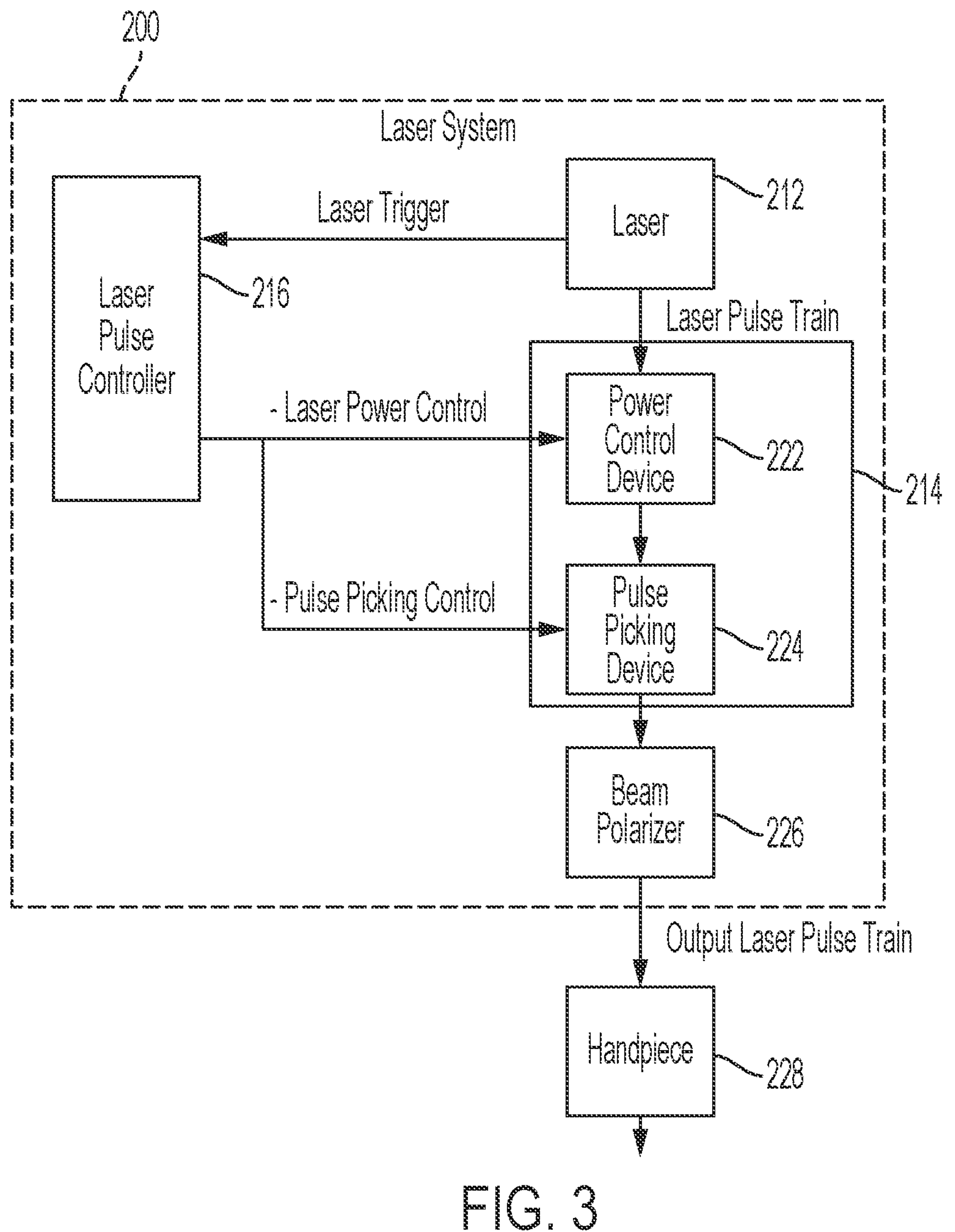
FIG. 3 shows an example of a laser system with components of an optical switching device.

FIG. 3 shows an example of a laser system 200 with components of an optical switching device 214. In the illustrated example, the optical switching device 214 comprises a power control device 222 and a pulse picking device 224. The pulse picking device 224 may comprise any suitable pulse picking device, including but not limited to a shutter-based pulse picking device as described above. The power control device 222 may comprise any suitable power control device, including but not limited to a waveplate-based power control device as described above. In alternative embodiments, a pockels cell arrangement may serve as the pulse picking device 224 and/or the power control device 222. The laser system 200 may further comprise a beam polarizer 226. The laser pulse controller 216 sends laser power control signals and pulse picking control signals to the optical switching device 214. As described above, a handpiece 228 may be connected, e.g., by a cable with an optical fiber, to an output port of the laser system 200. The output laser pulse train from the laser system 200 travels through the optical fiber and handpiece 228 to the target (e.g., cataractous lens, trabecular meshwork, scleral tissue, other tissue, etc.).

Figure 4:
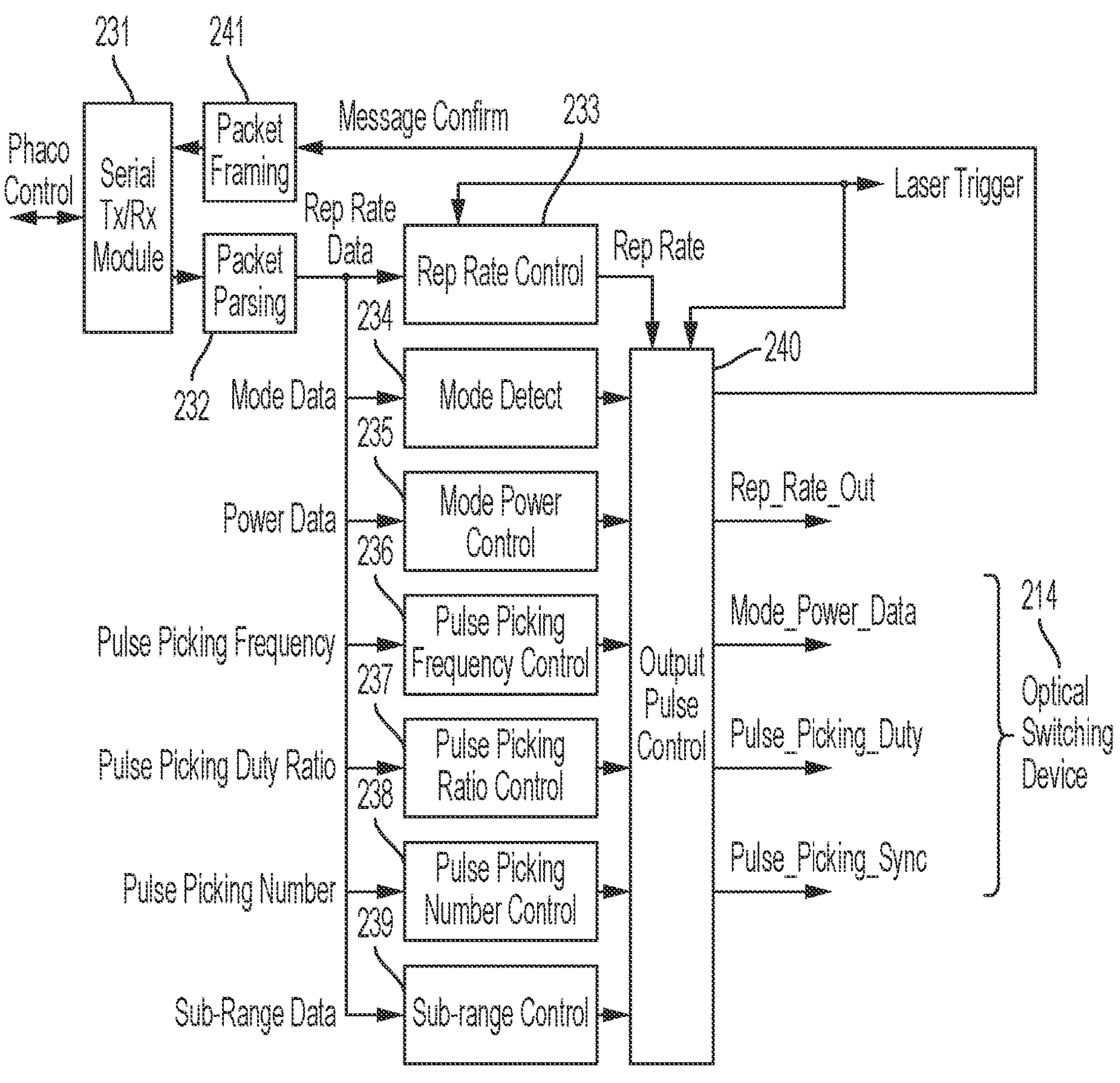
FIG. 4 shows an example of architecture for a laser pulse controller.

FIG. 4 shows an example of architecture for a laser pulse controller 216. As would be understood by persons having ordinary skill in the art, the use of controllers in processing environments may be implemented in software, firmware, hardware or some suitable combination of software, firmware, and/or hardware, such as software loaded into a processor and executed. The laser pulse controller 216 may be implemented in software, firmware, hardware or some suitable combination of software, firmware, and/or hardware, such as software loaded into a processor and executed.

The example laser pulse controller 216 comprises a serial transmitter/receiver (Tx/Rx) module 231 that communicates with a serial communication (Tx/Rx) controller or similar device (e.g., similar UART, CAN Bus, or Ethernet device) of the surgical console 100. In use, the surgical console 100 sends packets of data to the laser pulse controller 216, which are received by the serial Tx/Rx module 231. As described in more detail below, the packets may include data based, at least in part, on input from the adjustable input device 106. A packet parsing module 232 of the laser pulse controller 216 is configured to parse the packet data. In the illustrated example, the packet parsing module 232 sends repetition rate data to a repetition rate control module 233, mode data to a mode detect module 234, power data to a mode power control module 235, pulse picking frequency data to a pulse picking frequency control module 236, pulse picking duty ratio data to a pulse picking ratio control module 237, pulse picking number data to a pulse picking number control module 238, and sub-range data to a sub-range control module 239. The repetition rate control module 233 also receives a laser trigger input signal, indicating the timing of the beginning of each laser pulse. The repetition rate control module 233 sends signals indicating the repetition rate of the laser to an output pulse control module 240, which may also receive a laser trigger input signal. The output pulse control module 240 also receives input signals from the mode detect module 234, mode power control module 235, pulse picking frequency control module 236, pulse picking ratio control module 237, pulse picking number control module 238, and sub-range control module 239 based on their respective input data.

The output pulse control module 240 of the laser pulse controller 216 sends optical switching control signals to the optical switching device 214, wherein the optical switching control signals may be based, at least in part, on input from the adjustable input device 106. The optical switching control signals communicated by the laser pulse controller 216 to the optical switching device 214 may comprise a pulse picking rate signal (e.g., a Pulse_Picking_Sync signal, or a Pulse_Picking_Out signal), which controls the length of a pulse picking cycle. For example, the pulse picking rate signal may be a sync signal (e.g., Pulse_Picking_Sync) that is a timing signal corresponding to the pulse picking rate, e.g., a signal that marks the start of each pulse picking cycle. The optical switching control signals communicated by the laser pulse controller 216 to the optical switching device 214 may also comprise a pulse control signal (e.g., a Pulse_Picking_Duty signal, or a Pulse_Control_Out signal), which controls the percentage or number of laser pulses in each pulse picking cycle to be output from the laser system. The optical switching control signals communicated by the laser pulse controller 216 to the optical switching device 214 may also comprise a power level signal (e.g., a Mode_Power_Data signal, or a Mode_Power_Out signal), which controls the amount of energy of the laser pulses to be output from the laser system. A repetition rate signal (e.g., Rep_Rate_Out) may be sent to control the repetition rate of the laser pulses emitted by the laser.

As described in more detail below, the pulse control signal (e.g., Pulse_Picking_Duty) may enable output of a range of pulses in each pulse picking cycle. As described in more detail below, the number of laser pulses in each pulse picking cycle to be output from the laser system may be adjustable in a range that includes more than 50% of the laser pulses in each pulse picking cycle. In some embodiments, the number of laser pulses in each pulse picking cycle to be output from the laser system may be adjustable in a range from 0% to 100% of the laser pulses in each pulse picking cycle. In some embodiments, when the laser system is set so that the number of laser pulses emitted by the laser in each pulse picking cycle is N, the number of laser pulses in each pulse picking cycle to be output from the laser system may be adjustable in a range that includes 1 and N−1, and optionally 0 and/or N (e.g., a range from 0 to N, from 1 to N, from 0 to N−1, from 1 to N−1, etc.). For example, when the laser system is set so that the number of laser pulses emitted by the laser in each pulse picking cycle is 10, the number of laser pulses in each pulse picking cycle to be output from the laser system may be adjustable in a range that includes 1 and 9, and in some embodiments 0 and/or 10. As another example, when the laser system is set so that the number of laser pulses emitted by the laser in each pulse picking cycle is 16, the number of laser pulses in each pulse picking cycle to be output from the laser system may be adjustable in a range that includes 1 and 15, and in some embodiments 0 and/or 16.

The output pulse control module 240 of the laser pulse controller 216 may also send message confirm signals to a packet framing module 241. The packet framing module 241 assembles the data from the message confirm signal and sends it as packets of data to the serial Tx/Rx module 231. The Tx/Rx module 231 then sends the packets of data based on the message confirm signals to the serial Tx/Rx controller of the surgical console 100 to confirm the signals from the laser pulse controller 216.

Figures 5, 6:
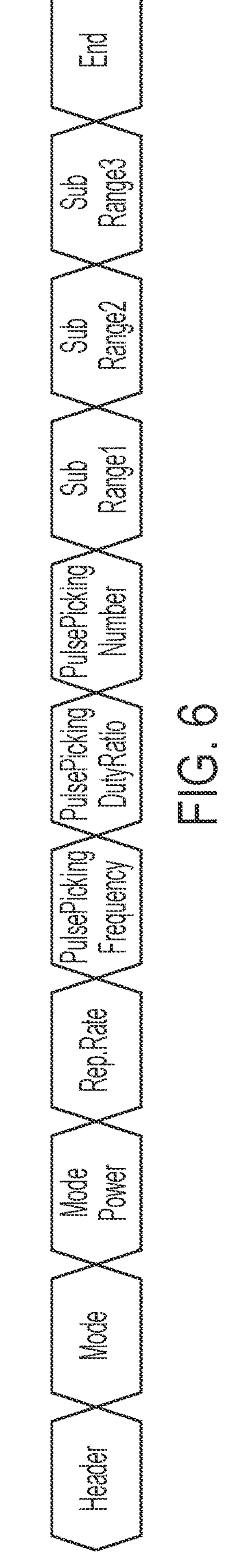
FIG. 5 shows an example operating range for an adjustable input device such as a foot pedal.
FIG. 6 shows an example packet of instructions for sending to a laser pulse controller.

FIG. 5 shows an example operating range for an adjustable input device such as a foot pedal 106. The foot pedal 106 or other adjustable input device can be actuated by an operator over the operating range to control the laser output. In the example of a foot pedal, the operator depresses the foot pedal by the desired amount to move the foot pedal into the desired area of the operating range. In other examples, such as hand-operated buttons or knobs, the operator moves or tunes the input device into the desired area of the operating range. In some embodiments, the foot pedal or other adjustable input device may be adjustable in real time during a surgical procedure, giving the operator the ability to dynamically control the laser pulses being output from the laser system during a procedure.

Many examples of different functioning over the operating range are possible. In the illustrated example, the operating range includes three subranges, but more or fewer subranges may be used.

The following is a description of one of many examples. When the adjustable input device is moved or tuned to subrange 1, the surgical console may be activated for a specific function, such as irrigation, without any laser output. When the adjustable input device is moved or tuned to subrange 2, the surgical console may be activated for a different function, such as aspiration, without any laser output. The irrigation function may continue to operate in subrange 2. When the adjustable input device is moved or tuned to subrange 3, the laser system may be activated to output laser electromagnetic energy. The irrigation and/or aspiration functions may continue to operate in subrange 3. By moving or tuning the adjustable input device within subrange 3, the operator may dynamically adjust the laser output, as described below.

Many variations are possible. For example, subrange 2 and 3 in the above example may be reversed, such that laser control occurs in subrange 2 and aspiration occurs in subrange 3.

In one example, adjustment of the adjustable input device controls the percentage of electromagnetic energy of the laser pulses that are output. That is, the laser emits laser pulses at a specific energy, and the input from the adjustable input device is used to adjust the laser energy control system of the optical switching device 214 to control the percentage of energy of the laser pulses that are output from the laser system. Based on the input from the adjustable input device, the power level signal (e.g., Mode_Power_Data), which is sent by the laser pulse controller 216 to the optical switching device 214, may be adjusted to control the amount of energy of the laser pulses output from the laser system. For example, the top of subrange 3 may correspond to 0% of laser energy output, the bottom of subrange 3 may correspond to 100% of laser energy output, and positions in between may correspond to increments in the range of 0% to 100%. In other examples, the operating range of the adjustable input device is configured to allow an operator to control dynamically the percentage of laser pulses emitted from the laser that are output from the laser system. In other examples, adjusting the adjustable input device into subrange 3, or to a specific point in subrange 3, can act as an on-off switch that triggers operation of the laser system at the set output.

One or more inputs to the system, e.g., from a touchscreen (with graphical user interface), button, dial, knob, foot pedal, adjustable input device, or other input device, may be used to control the laser system to output only certain of the laser pulses emitted by the laser. That is, the laser emits laser pulses at a specific repetition rate, and the input is used to control the optical switching device 214 to switch back and forth between the first condition in which it allows laser pulses emitted from the laser to be output from the laser system and the second condition in which it prevents laser pulses emitted from the laser from being output from the laser system. One or more of the inputs to the system may comprise or be part of the console 100, the adjustable input device 106, and/or an external control system (e.g., with its own touchscreen (with graphical user interface), button, dial, knob, or other input device).

In certain embodiments, a user input controls a pulse picking frequency, which controls the length of a pulse picking cycle, and a pulse picking duty ratio. Based on the input, the laser pulse controller sends signals (e.g., Pulse_Picking_Sync and Pulse_Picking_Duty signals) to the optical switching device and controls the pulse picking cycle and the number of laser pulses in each pulse picking cycle to be output from the laser system. For example, if the repetition rate of the laser is 1000 Hz, a pulse picking rate of 100 Hz results in 10 pulses per cycle. By selecting input that controls the pulse picking duty ratio, a range of different pulses per cycle may be output (e.g., a range from 1 to 9, from 1 to 10, from 0 to 9, from 0 to 10, etc.), thereby controlling the percentage of laser pulses that are output.

In some examples, the repetition rate of the laser and the energy output of the laser, including different energy outputs of the laser, if desired, may also be selected by the adjustable input device or another input device, such as a touchscreen, button, dial, knob, or other input.

FIG. 6 shows an example packet of instructions for sending to a laser pulse controller. The packet includes the following data: Header, Mode, Mode Power, Repetition Rate, Pulse Picking Frequency, Pulse Picking Duty Ratio, Pulse Picking Number, Subrange 1, Subrange 2, Subrange 3, and End. The Header identifies the beginning of the packet. The Mode identifies which operating mode has been selected. The Mode Power identifies the selected power output of the laser. The Repetition Rate identifies the rate of pulses to be emitted from the laser. The Pulse Picking Frequency identifies the length of a pulse picking cycle. The Pulse Picking Duty Ratio identifies what number or percentage of pulses in each pulse picking cycle are to be output. The Pulse Picking Number identifies the maximum number of laser pulses that may be selected in each pulse picking cycle. Subrange 1, Subrange 2, and Subrange 3 identify the position to which the adjustable input device has been moved or tuned, including the incremental position within the range (e.g., 0 to 100).

Figures 7A, 7B, 7C:
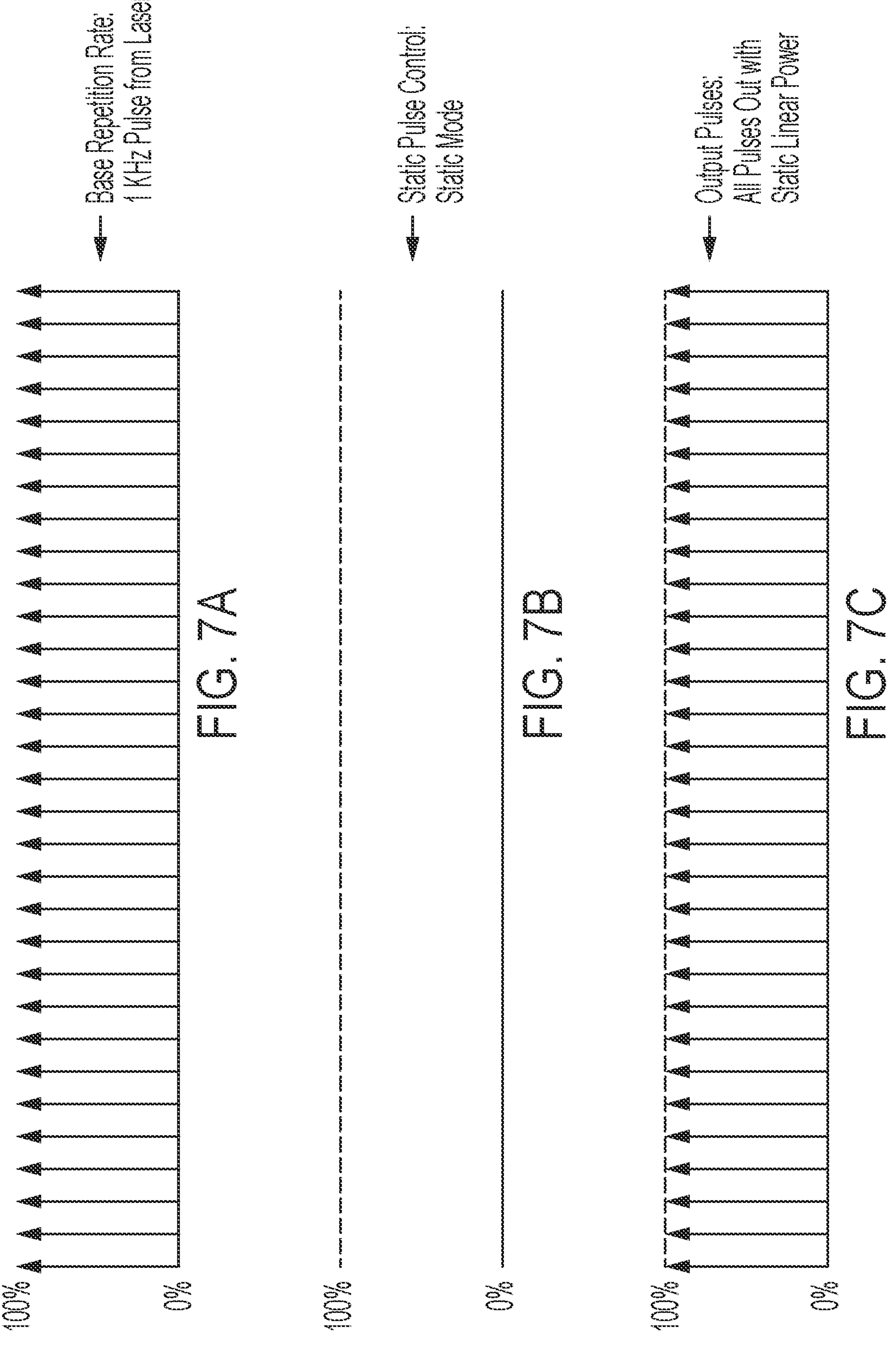
FIG. 7A shows an example of laser pulses emitted from a laser.
FIG. 7B shows an example of a static pulse control signal.
FIG. 7C shows the output of laser pulses in accordance with the static pulse control signal of FIG. 7B.

FIG. 7A shows an example of laser pulses emitted from a laser, each upward arrow representing a laser pulse. This shows the repetition rate of the laser pulses being emitted by the laser, which in this example is 1 KHz.

FIG. 7B shows an example of a static pulse control signal. The power level signal (e.g., Mode_Power_Data) is set at 100%. In static mode, as shown, this power level is constant. In variable mode, this power level is adjustable, e.g., by the adjustable input device (e.g., foot pedal).

FIG. 7C shows the output of laser pulses in accordance with the static pulse control signal of FIG. 7B. As can be seen, all laser pulses are output, at 100% power.

Figures 8A, 8B, 8C:
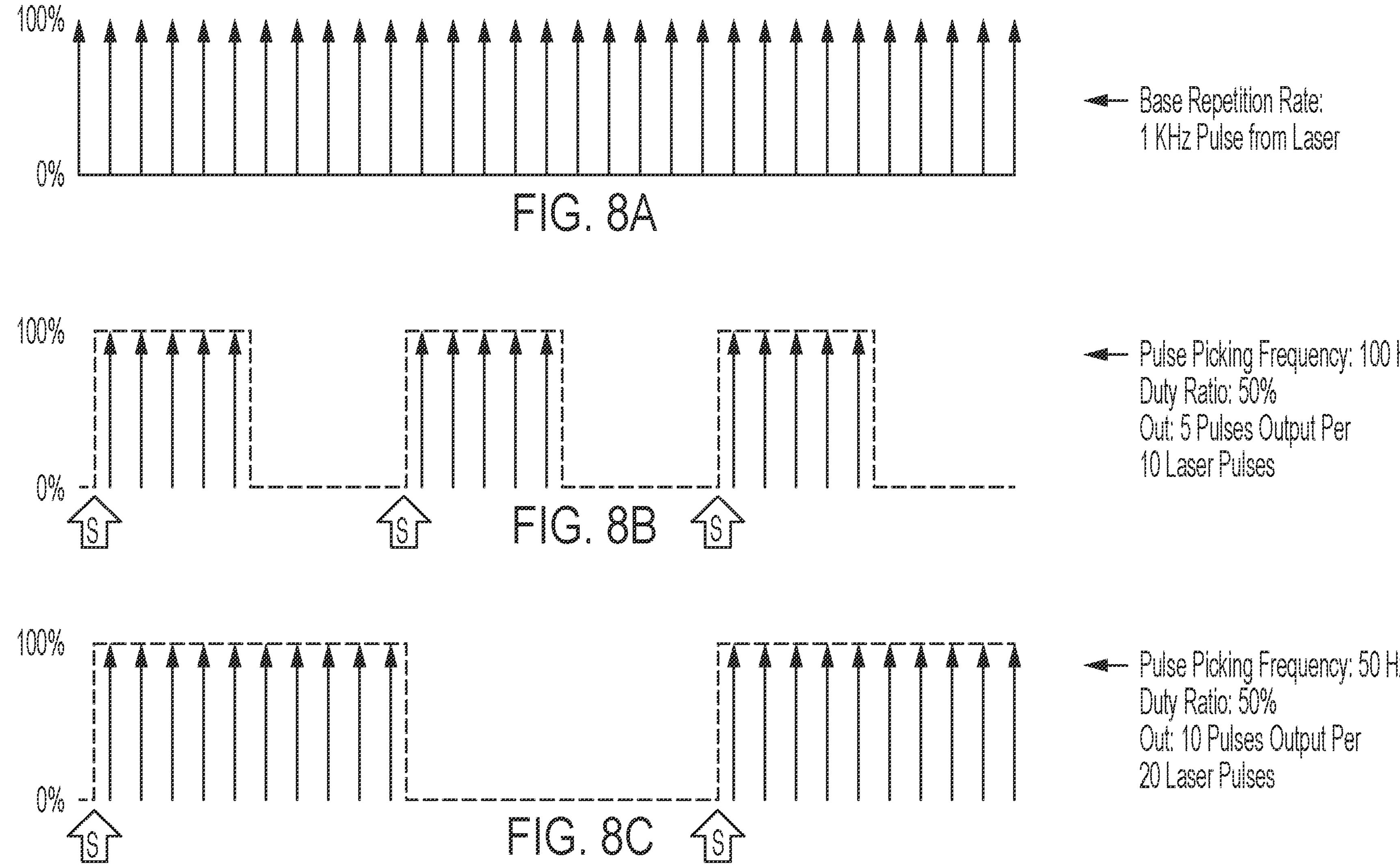
FIG. 8A shows an example of laser pulses emitted from a laser, similar to FIG. 7A.
FIG. 8B shows an example of a first pulse picking frequency wherein 50% of the pulses emitted by the laser are output from the laser system.
FIG. 8C shows an example of a second pulse picking frequency wherein 50% of the pulses emitted by the laser are output from the laser system.

FIG. 8A shows an example of laser pulses emitted from a laser, similar to FIG. 7A. Like FIG. 7A, this shows the repetition rate of the laser pulses being emitted by the laser, which in this example is 1 KHz.

FIG. 8B shows an example of a first pulse picking frequency wherein 50% of the pulses emitted by the laser are output from the laser system. The pulse picking frequency in this example is 100 Hz, which with a 1 KHz repetition rate results in 10 laser pulses per pulse picking cycle. The pulse picking frequency can be established by a sync signal (e.g., Pulse_Picking_Sync), identified by the arrow labeled S, that marks the beginning of each pulse picking cycle. At a duty ratio of 50%, this results in 5 pulses per pulse picking cycle being output from the system. That is, 5 laser pulses are output, followed by 5 laser pulses that are not output, and this pattern is repeated.

FIG. 8C shows an example of a second pulse picking frequency wherein 50% of the pulses emitted by the laser are output from the laser system. The pulse picking frequency in this example is 50 Hz, which with a 1 KHz repetition rate results in 20 laser pulses per pulse picking cycle. As in FIG. 8B, the pulse picking frequency can be established by a sync signal (e.g., Pulse_Picking_Sync), identified by the arrow labeled S, that marks the beginning of each pulse picking cycle. At a duty ratio of 50%, this results in 10 pulses per pulse picking cycle being output from the system. That is, 10 laser pulses are output, followed by 10 laser pulses that are not output, and this pattern is repeated.

The operating modes in FIGS. 7A-7C and 8A-8C are similar in output to operating modes described and illustrated in U.S. Provisional Patent Application No. 63/256,071, the entirety of which is hereby incorporated by reference herein. For example, FIG. 7C shows an output similar to sculpt mode described and illustrated in that application, while FIGS. 8B and 8C show outputs similar to quad mode described and illustrated in that application. FIGS. 9A-9D and 10A-10D illustrate how embodiments herein allow additional flexibility in the percentage of laser pulses that may be output in each pulse picking cycle. With certain embodiments herein, the number of laser pulses in each pulse picking cycle to be output from the laser system is adjustable in a range that includes more than 50% of the laser pulses in each pulse picking cycle. With certain embodiments herein, up to 100% of the laser pulses in a pulse picking cycle may be output. When operated at 100% of the laser pulses being output, such embodiments are analogous to embodiments in sculpt mode. When operated at less than 100% of the laser pulses being output, such embodiments are analogous to embodiments in quad mode.

Figures 9A, 9B, 9C, 9D:
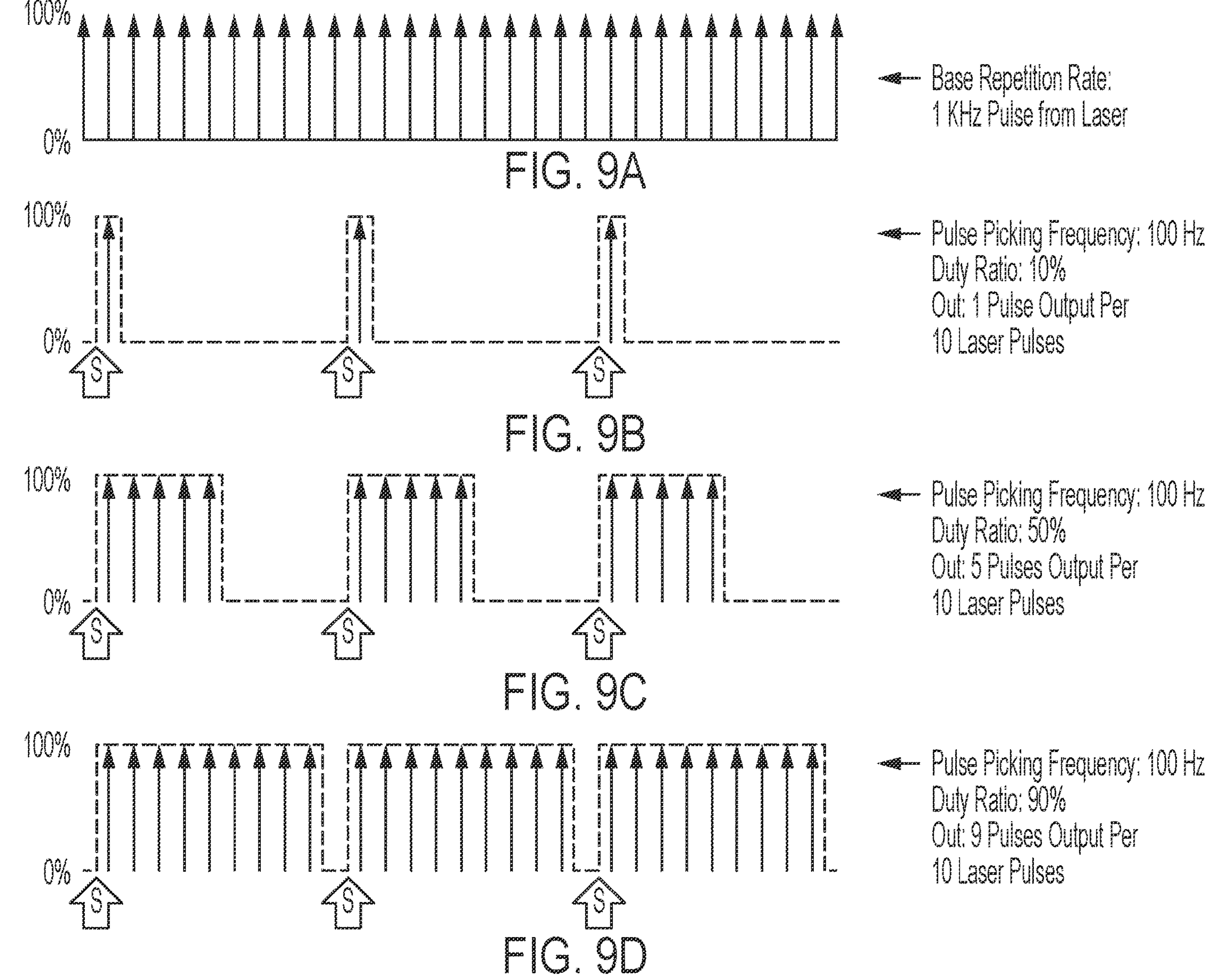
FIG. 9A shows an example of laser pulses emitted from a laser, similar to FIGS. 7A and 8A.
FIG. 9B shows an example wherein the laser system is adjusted to output 1 out of every 10 laser pulses emitted by the laser.
FIG. 9C shows an example wherein the laser system is adjusted to output 5 out of every 10 laser pulses emitted by the laser.
FIG. 9D shows an example wherein the laser system is adjusted to output 9 out of every 10 laser pulses emitted by the laser.

FIG. 9A shows an example of laser pulses emitted from a laser, similar to FIGS. 7A and 8A. Like FIGS. 7A and 8A, this shows the repetition rate of the laser pulses being emitted by the laser, which in this example is 1 KHz.

FIG. 9B shows an example wherein the laser system is adjusted to output 1 out of every 10 laser pulses emitted by the laser. The pulse picking frequency in this example is 100 Hz, which with a 1 KHz repetition rate results in 10 laser pulses per pulse picking cycle. The pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 9B, the duty ratio is 10%, or 1 out of 10 pulses. This results in 1 pulse per pulse picking cycle being output from the system. That is, 1 laser pulse is output, followed by 9 laser pulses that are not output, and this pattern is repeated.

FIG. 9C shows an example wherein the laser system is adjusted to output 5 out of every 10 laser pulses emitted by the laser. As in FIG. 9B, the pulse picking frequency in this example is 100 Hz, which with a 1 KHz repetition rate results in 10 laser pulses per pulse picking cycle. As in FIG. 9B, the pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 9C, the duty ratio is 50%, or 5 out of 10 pulses. This results in 5 pulses per pulse picking cycle being output from the system. That is, 5 laser pulses are output, followed by 5 laser pulses that are not output, and this pattern is repeated.

FIG. 9D shows an example wherein the laser system is adjusted to output 9 out of every 10 laser pulses emitted by the laser. As in FIGS. 9B and 9C, the pulse picking frequency in this example is 100 Hz, which with a 1 KHz repetition rate results in 10 laser pulses per pulse picking cycle. As in FIGS. 9B and 9C, the pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 9D, the duty ratio is 90%, or 9 out of 10 pulses. This results in 9 pulses per pulse picking cycle being output from the system. That is, 9 laser pulses are output, followed by 1 laser pulse that is not output, and this pattern is repeated.

Figures 10A, 10B, 10C, 10D:
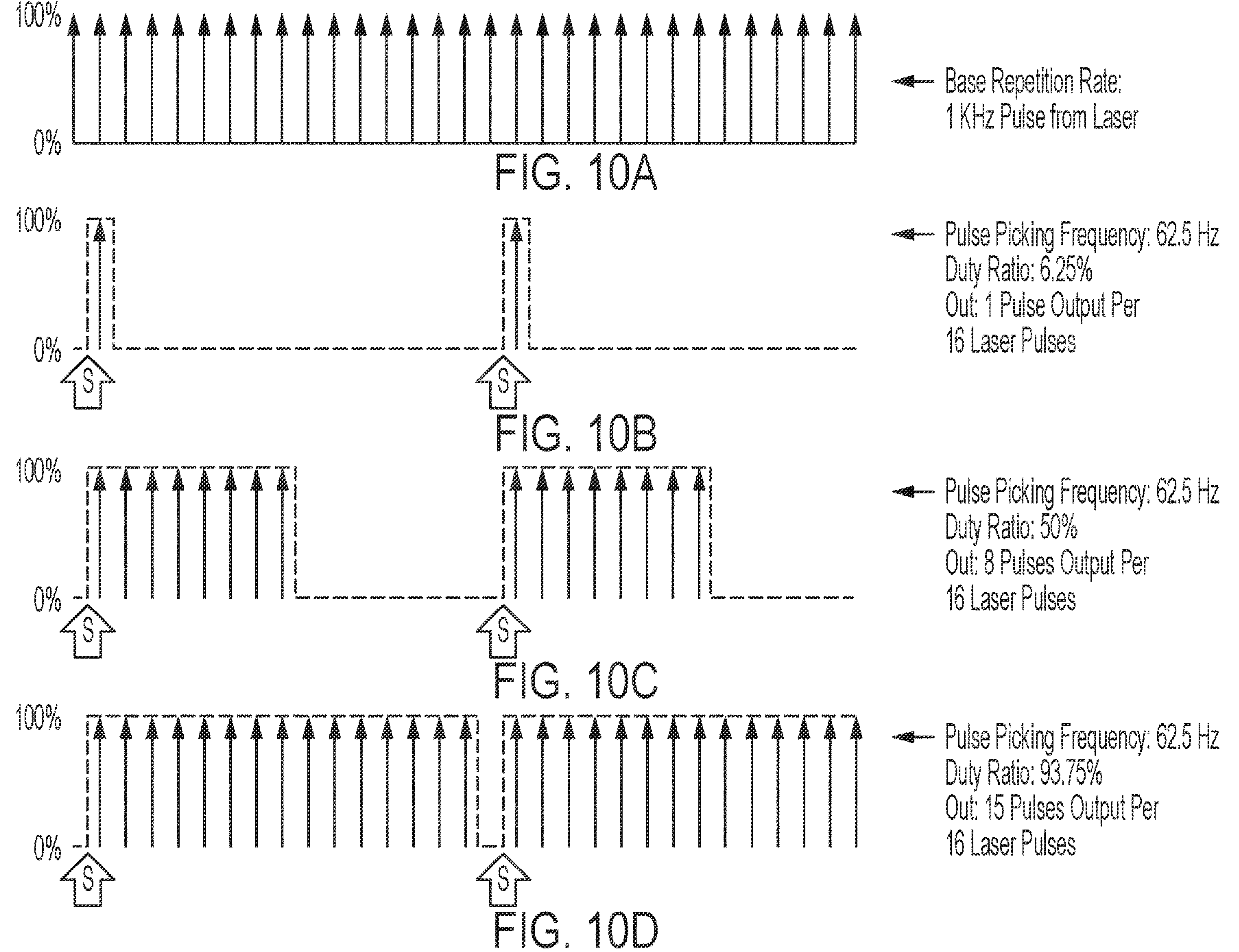
FIG. 10A shows an example of laser pulses emitted from a laser, similar to FIGS. 7A, 8A, and 9A.
FIG. 10B shows an example wherein the laser system is adjusted to output 1 out of every 16 laser pulses emitted by the laser.
FIG. 10C shows an example wherein the laser system is adjusted to output 8 out of every 16 laser pulses emitted by the laser.
FIG. 10D shows an example wherein the laser system is adjusted to output 15 out of every 16 laser pulses emitted by the laser.

FIG. 10A shows an example of laser pulses emitted from a laser, similar to FIGS. 7A, 8A, and 9A. Like FIGS. 7A, 8A, and 9A, this shows the repetition rate of the laser pulses being emitted by the laser, which in this example is 1 KHz.

FIG. 10B shows an example wherein the laser system is adjusted to output 1 out of every 16 laser pulses emitted by the laser. The pulse picking frequency in this example is 62.5 Hz, which with a 1 KHz repetition rate results in 16 laser pulses per pulse picking cycle. The pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 10B, the duty ratio is 6.25%, or 1 out of 16 pulses. This results in 1 pulse per pulse picking cycle being output from the system. That is, 1 laser pulse is output, followed by 15 laser pulses that are not output, and this pattern is repeated.

FIG. 10C shows an example wherein the laser system is adjusted to output 8 out of every 16 laser pulses emitted by the laser. As in FIG. 10B, the pulse picking frequency in this example is 62.5 Hz, which with a 1 KHz repetition rate results in 16 laser pulses per pulse picking cycle. As in FIG. 10B, the pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 10C, the duty ratio is 50%, or 8 out of 16 pulses. This results in 8 pulses per pulse picking cycle being output from the system. That is, 8 laser pulses are output, followed by 8 laser pulses that are not output, and this pattern is repeated.

FIG. 10D shows an example wherein the laser system is adjusted to output 15 out of every 16 laser pulses emitted by the laser. As in FIGS. 10B and 10C, the pulse picking frequency in this example is 62.5 Hz, which with a 1 KHz repetition rate results in 16 laser pulses per pulse picking cycle. As in FIGS. 10B and 10C, the pulse picking frequency can be established by a sync signal (e.g., Pulse_Picking_Sync), identified by the arrow labeled S, that marks the beginning of each pulse picking cycle. A duty ratio signal (e.g., Pulse_Picking_Duty) establishes the number or percentage of laser pulses in each pulse picking cycle that are permitted to be output from the system. In the example of FIG. 9D, the duty ratio is 93.75%, or 15 out of 16 pulses. This results in 15 pulses per pulse picking cycle being output from the system. That is, 15 laser pulses are output, followed by 1 laser pulse that is not output, and this pattern is repeated.

The maximum number of pulses that may be selected for output in each pulse picking cycle is based on both the repetition rate of the laser and the pulse picking rate. The following table shows, for repetition rates of 1100 Hz and 1000 Hz, and for certain example pulse picking rates, how adjustment of the pulse picking rate changes the maximum number of pulses that may be selected for output in each pulse picking cycle:

| Repetition Rate 1100 Hz | | | Repetition Rate 1000 Hz | | |
|---|---|---|---|---|---|
| Pulse Picking Rate (Hz) | 50% Duty Ratio (50% Pulses Per Cycle) | 1 to ~N Pulses Per Cycle | Pulse Picking Rate (Hz) | 50% Duty Ratio (50% Pulses Per Cycle) | 1 to ~N Pulses Per Cycle |
| 275 | 2 | 1 to ~4 | 250 | 2 | 1 to ~4 |
| 137.5 | 4 | 1 to ~8 | 125 | 4 | 1 to ~8 |
| 110 | 5 | 1 to ~10 | 100 | 5 | 1 to ~10 |
| 55 | 10 | 1 to ~20 | 62.5 | 8 | 1 to ~16 |
| 50 | 11 | 1 to ~22 | 50 | 10 | 1 to ~20 |
| 11 | 50 | 1 to ~100 | 20 | 25 | 1 to ~50 |
| 10 | 55 | 1 to ~110 | 10 | 50 | 1 to ~100 |
| 1 | 550 | 1 to ~1100 | 1 | 500 | 1 to ~1000 |
| 0.5 | 1100 | 1 to ~2200 | 0.5 | 1000 | 1 to ~2000 |
| 0.25 | 2200 | 1 to ~4400 | 0.25 | 2000 | 1 to ~4000 |
| 0.2 | 2750 | 1 to ~5500 | 0.2 | 2500 | 1 to ~5000 |

Any repetition rate suitable for the desired application may be used. As additional examples, the following table shows, for repetition rates of 1500 Hz and 2000 Hz, and for certain example pulse picking rates, how adjustment of the pulse picking rate changes the maximum number of pulses that may be selected for output in each pulse picking cycle:

| Repetition Rate 1500 Hz | | | Repetition Rate 2000 Hz | | |
|---|---|---|---|---|---|
| Pulse Picking Rate (Hz) | 50% Duty Ratio (50% Pulses Per Cycle) | 1 to ~N Pulses Per Cycle | Pulse Picking Rate (Hz) | 50% Duty Ratio (50% Pulses Per Cycle) | 1 to ~N Pulses Per Cycle |
| 375 | 2 | 1 to ~4 | 500 | 2 | 1 to ~4 |
| 250 | 3 | 1 to ~6 | 250 | 4 | 1 to ~8 |
| 150 | 5 | 1 to ~10 | 200 | 5 | 1 to ~10 |
| 125 | 6 | 1 to ~12 | 125 | 8 | 1 to ~16 |
| 75 | 10 | 1 to ~20 | 100 | 10 | 1 to ~20 |
| 50 | 15 | 1 to ~30 | 50 | 20 | 1 to ~40 |
| 30 | 25 | 1 to ~50 | 40 | 25 | 1 to ~50 |
| 25 | 30 | 1 to ~60 | 25 | 40 | 1 to ~80 |
| 15 | 50 | 1 to ~100 | 10 | 100 | 1 to ~200 |
| 10 | 75 | 1 to ~150 | 5 | 200 | 1 to ~400 |
| 1 | 750 | 1 to ~1500 | 1 | 1000 | 1 to ~2000 |
| 0.5 | 1500 | 1 to ~3000 | 0.5 | 2000 | 1 to ~4000 |
| 0.25 | 3000 | 1 to ~6000 | 0.25 | 4000 | 1 to ~8000 |
| 0.2 | 3750 | 1 to ~7500 | 0.2 | 5000 | 1 to ~10000 |

By selecting and/or adjusting the repetition rate, pulse picking rate, and pulse picking duty ratio, any desired sequence of allowing laser pulses to be output and preventing laser pulses from being output may be selected. The adjustable input device and systems and methods disclosed herein enable the operator to have flexible control over laser pulse output.

An example method of controlling a surgical system as described herein is as follows. An operator selects inputs for the operating mode, maximum power, repetition rate of the laser, pulse picking rate, and duty ratio. In some embodiments, certain options may be provided for selection, wherein dependent on the selection by the operator, the surgical system sets the operating mode, maximum power, repetition rate of the laser, pulse picking rate, and/or duty ratio. Alternatively, any of these parameters may be preset. The operator operates the system, with the laser output of a handpiece directed at the desired location (e.g., a cataractous lens, trabecular meshwork, scleral tissue, other tissue, etc.). Based on the input(s), and optionally other parameters, control signals are sent (e.g., by a packet as in FIG. 6) to a laser pulse controller. Based on the input, the laser pulse controller sends optical switching control signals to the optical switching device to control the laser output. The laser emits electromagnetic radiation from a laser in laser pulses. Based on the input(s), the optical switching device selectively allows certain laser pulses to be output and prevents certain laser pulses from being output. In some embodiments, the operator may actuate the adjustable input device (e.g., foot pedal) over an operating range to control dynamically the power of the laser pulses being output from the laser system.

The optical switching control signals may comprise a pulse picking frequency signal controlling the length of a pulse picking cycle and a pulse picking duty ratio signal controlling the number of laser pulses in each pulse picking cycle to be output from the laser system. The operator may dynamically adjust the adjustable input device in real time to adjust the power output, i.e., the power level signal may be based on dynamic input from the adjustable input device. The operator may dynamically adjust the adjustable input device in real time to adjust the power level signal and, consequently, the amount of energy of the laser pulses to be output from the laser system. In other examples, the operator may dynamically adjust the adjustable input device in real time to adjust the number or percentage of laser pulses emitted from the laser that are output from the laser system.

The operator may switch inputs. The selected inputs may be based on the type of procedure, the stage of the procedure, the conditions, or other factors.

The ability to selectively output laser pulses and/or to control the laser output energy is useful for procedures in which laser control is advantageous. For example, in cataract surgery, it may be desirable to operate the laser system with high power for initially breaking up the lens. It may be desirable to operate the laser system with lower power for breaking up smaller pieces, so a lower energy level may be preferred. Pulse number control and/or pulse energy level control of laser pulses allows for a correct level of force to be applied to smaller particles which might otherwise be pushed away before they can be aspirated out of the eye by the irrigation system of the hand piece. As another example, for glaucoma treatment, it may be desirable to operate the laser system with a single laser pulse or just a few laser pulses for formation of a channel through eye tissue. The longer pulse picking frequencies may be desirable for such procedures. For example, with a long pulse picking cycle and a low duty ratio, the system can be configured such that the operator can emit one or only a few laser pulses at a time. For example, in some embodiments, the operator can use the foot pedal to emit one or only a few laser pulses at a time. It may also be desirable to use soft or low energy for certain glaucoma procedures.

As would be understood by persons of ordinary skill in the art, systems and methods as disclosed herein have advantages over prior systems and methods. For example, systems and methods as described herein allow simple, flexible, and/or dynamic control of laser pulses and/or energy, improving the ease, time, efficiency, accuracy, outcome, and/or cost of the procedures.

Persons of ordinary skill in the art will appreciate that the embodiments encompassed by the disclosure are not limited to the particular example embodiments described above. While illustrative embodiments have been shown and described, a wide range of modification, change, and substitution is contemplated in the foregoing disclosure. It is understood that such variations may be made to the foregoing without departing from the scope of the disclosure. Accordingly, it is appropriate that the appended claims be construed broadly and in a manner consistent with the disclosure.

What is claimed is:

1. A surgical system comprising:

a laser configured to emit electromagnetic radiation in laser pulses;

an optical switching device configured to switch between a first condition in which it allows laser pulses emitted from the laser to be output from the surgical system and a second condition in which it prevents laser pulses emitted from the laser from being output from the surgical system; and a laser pulse controller configured to communicate optical switching control signals to the optical switching device;

wherein the optical switching control signals communicated by the laser pulse controller control a length of a pulse picking cycle and a number of laser pulses in each pulse picking cycle to be output from the surgical system; and wherein the number of laser pulses in each pulse picking cycle to be output from the surgical system is adjustable in a range that includes more than 50% of the laser pulses in each pulse picking cycle;

wherein the optical switching control signals communicated by the laser pulse controller comprise a first signal that controls the length of a pulse picking cycle and a second signal that controls the number of laser pulses in each pulse picking cycle to be output from the surgical system;

wherein the first signal is a sync signal that is a timing signal that marks a start of each pulse picking cycle;

wherein pulse picking cycle comprises a number of laser pulses to be output from the surgical system, indicated by the second signal, followed by a number of laser pulses left in the pulse picking cycle that are not output from the surgical system;

wherein the number of pulses to be output from the surgical system, as indicated by the second signal, in each pulse picking cycle is greater than 50% of a total number of pulses in the pulse picking cycle but less than a total number of pulses in the pulse picking cycle.

2. The surgical system as recited in claim 1, wherein the optical switching device is further configured to control an amount of energy of the laser pulses emitted from the laser that is output from the surgical system.

3. The surgical system as recited in claim 1, further comprising an adjustable input device configured to be actuated over an operating range.

4. The surgical system as recited in claim 3, wherein the operating range of the adjustable input device is configured to allow an operator to control dynamically an amount of energy of the laser pulses emitted from the laser that is output from the surgical system.

5. The surgical system as recited in claim 3, wherein the operating range of the adjustable input device is configured to allow an operator to control dynamically a percentage of laser pulses emitted from the laser that are output from the surgical system.

6. The surgical system as recited in claim 3, wherein the adjustable input device comprises a foot pedal configured to be actuated over the operating range.

7. The surgical system as recited in claim 1, wherein the optical switching device further comprises a laser energy control system configured to regulate an amount of electromagnetic energy of each laser pulse that exits the surgical system.

8. A method of controlling a surgical system comprising:

(i) providing input to the surgical system, wherein the surgical system comprises:

a laser configured to emit electromagnetic radiation in laser pulses;

an optical switching device configured to switch between a first condition in which it allows laser pulses emitted from the laser to be output from the surgical system and a second condition in which it prevents laser pulses emitted from the laser from being output from the surgical system; and a laser pulse controller configured to communicate optical switching control signals to the optical switching device;

wherein the input to the surgical system comprises input that controls a length of a pulse picking cycle and a number of laser pulses in each pulse picking cycle to be output from the surgical system;

wherein the number of laser pulses in each pulse picking cycle to be output from the surgical system is adjustable in a range that includes more than 50% of the laser pulses in each pulse picking cycle;

(ii) emitting electromagnetic radiation from a laser in laser pulses; and (iii) outputting laser pulses from the surgical system in accordance with the input that controls the length of a pulse picking cycle and the number of laser pulses in each pulse picking cycle to be output from the surgical system;

wherein the optical switching control signals communicated by the laser pulse controller comprise a first signal that controls the length of a pulse picking cycle and a second signal that controls the number of laser pulses in each pulse picking cycle to be output from the surgical system;

wherein the first signal is a sync signal that is a timing signal that marks a start of each pulse picking cycle;

wherein pulse picking cycle comprises a number of laser pulses to be output from the surgical system, indicated by the second signal, followed by a number of laser pulses left in the pulse picking cycle that are not output from the surgical system;

wherein the number of pulses to be output from the surgical system, as indicated by the second signal, in each pulse picking cycle is greater than 50% of a total number of pulses in the pulse picking cycle but less than a total number of pulses in the pulse picking cycle.

9. The method of controlling a surgical system as recited in claim 8, wherein the step of outputting laser pulses from the surgical system in accordance with the input comprises controlling a percentage of laser pulses emitted from the laser that are output from the surgical system.

10. The method of controlling a surgical system as recited in claim 8, wherein the step of outputting laser pulses from the surgical system in accordance with the input comprises controlling an amount of energy of the laser pulses emitted from the laser that is output from the surgical system.

* * * * *